(12) United States Patent
Lau et al.

(10) Patent No.: US 9,216,942 B2
(45) Date of Patent: Dec. 22, 2015

(54) COMPOUNDS AND USES THEREOF FOR TREATING INFLAMMATION AND MODULATING IMMUNE RESPONSES

(71) Applicants: PURAPHARM COMPANY LIMITED, Hong Kong (CN); VERSITECH LIMITED, Hong Kong (CN)

(72) Inventors: Allan Sik Yin Lau, Hong Kong (CN); Lai Hung Cindy Yang, Hong Kong (CN); Stanley Chi Chung Chik, Hong Kong (CN)

(73) Assignees: BAGI RESEARCH LIMITED, Hong Kong (CN); VERSITECH LIMITED, Hong Kong (CN)

( * ) Notice: Subject to any disclaimer, the term of this patent is extended or adjusted under 35 U.S.C. 154(b) by 12 days.

(21) Appl. No.: 13/790,707

(22) Filed: Mar. 8, 2013

(65) Prior Publication Data

US 2013/0237599 A1 Sep. 12, 2013

Related U.S. Application Data

(60) Provisional application No. 61/608,347, filed on Mar. 8, 2012.

(51) Int. Cl.
 C07C 69/734 (2006.01)
 C07C 69/732 (2006.01)

(52) U.S. Cl.
 CPC ............. *C07C 69/734* (2013.01); *C07C 69/732* (2013.01)

(58) Field of Classification Search
 None
 See application file for complete search history.

(56) References Cited

U.S. PATENT DOCUMENTS

2010/0184856 A1* 7/2010 Lau et al. ...................... 514/543

FOREIGN PATENT DOCUMENTS

| JP | 2006 029571 A | 2/2005 |
| WO | WO 2010/079406 A1 | 7/2010 |
| WO | WO 2012/014085 A2 | 2/2012 |

OTHER PUBLICATIONS

Lippard. The art of chemical synthesis, Nature (2002), vol. 416, pp. 587.*
Chen et al. Cimiracemates A-D, phenylpropanoid esters from the rhizomes of Cimicifuga racemosa. Phytochemistry (2002), vol. 61, pp. 409-413.*
Patani et al. Bioisosterism: A Rational Approach in Drug Design. Chem. Rev. (1996), vol. 96, pp. 3147-3176.*
Abate, A. et al., "Lipopolysaccharide-induced expression of cyclookygenase-2 in mouse macrophages is inhibited by chloromethylketones and a direct inhibitor of NF_$\kappa$B translocation," 1998, *Prostaglandins Other Lipid Mediators*, vol. 56, p. 277-290.
Aggarwal, B. et al., "Inflammation and Cancer: How Hot is the Link?" 2006, *Biochemical Pharmacology: Science Direct*, vol. 72, p. 1605-1621.
Bone, R., "Gram-negative sepsis. Background, clinical features, and intervention," 1991, *Chest*, vol. 100, p. 802-808.
Chan-Hui, P. et al., "Human mitogen-activated protein kinase kinase kinase mediates the stress-induced activation of mitogen-activated protein kinase cascades," 1998, *Biochem. J.*, vol. 336 (pt. 3), p. 599-609.
Chen, F. et al., "New insights into the role of nuclear factor-$\kappa$B, a ubiquitous transcription factor in the initiation of diseases," 1999, *Clinical Chemistry*, vol. 45, p. 7-17.
Cheng, S. et al., "Interferon-$\gamma$ regulation of TNF$\alpha$-induced matrix metalloproteinase 3 expression and migration of human glioma T98G cells," 2007, *International Journal of Cancer*, vol. 121, p. 1190-1196.
Cheung, B. et al., "A role for double-stranded RNA-activated protein kinase PKR in Mycobacterium-induced cytokine expression," 2005, *J. Immunol.*, vol. 175, p. 7218-7225.
Clay, H. et al., "Tumor necrosis factor signaling mediates resistance to mycobacteria by inhibiting bacterial growth and macrophage death," 2008, *Immunity*, vol. 29, p. 283-294.
Davis, R., "The mitogen-activated protein kinase signal transduction pathway," 1993, *Journal of Biological Chemistry*, vol. 268, p. 14553-14556.
Herlaar, E. et al., "p38 MAPK signaling cascades in inflammatory disease," 1999, *Molecular Medicine Today*, vol. 5, p. 439-447.
Ichijo, H., "From receptors to stress-activated MAP kinases," 1999, *Oncogene*, vol. 18, p. 6087-6093.
Lee, D. et al., "p38 mitogen-activated protein kinase-dependent hyperinduction of tumor necrosis factor alpha expression in response to avian influenza virus H5N1," 2005, *Journal of Virology*, vol. 79, p. 10147-10154.
Li, J. et al., "Mechanisms for HIV Tat upregulation of IL-10 and other cytokine expression: kinase signaling and PKR-mediated immune response," 2005, *FEBS Lett.*, vol. 579, p. 3055-3062.
Montesano, R. et al., "Tumour necrosis factor $\alpha$ confers an invasive, transformed phenotype on mammary epithelial cells," 2005, *Journal of Cell Science*, vol. 118, p. 3487-3500.
Ohlsson, K. et al., "Interleukin-1 receptor antagonist reduces mortality from endotoxin shock," 1990, *Nature*, vol. 348, p. 550-552.
Pando, M. et al., "Signal-dependent and -independent degradation of free and NF-$\kappa$B-bound I$\kappa$B$\alpha$," 2000, *Journal of Biological Chemistry*, vol. 275, p. 21,278-21,286.
Panés, J. et al., "Crohn's disease: a review of current treatment with a focus on biologics," 2007, *Drugs*, vol. 67, p. 2511-2537.
Raetz, C, "Biochemistry of endotoxins," 1990, *Ann. Rev. Biochem.*, vol. 59, p. 129-170.
Raetz, C. et al., "Gram-negative endotoxin: an extraordinary lipid with profound effets on eukaryotic signal transduction," 1991, *The FASEB Journal*, vol. 5, p. 2652-2660.

(Continued)

*Primary Examiner* — Melenie McCormick
*Assistant Examiner* — Taina D Matos Negron
(74) *Attorney, Agent, or Firm* — Saliwanchik, Lloyd & Eisenschenk (57) ABSTRACT

The present invention provides compounds, and compositions comprising these compounds, which have immunomodulatory activity and/or anti-inflammatory activity.

5 Claims, 3 Drawing Sheets

(56) References Cited

OTHER PUBLICATIONS

Saunders, B. et al., "Life and death in the granuloma: immunopathology of tuberculosis," 2007, *Immunology and Cell Biology*, vol. 85, p. 103-111.

Shakhov, A. et al. "κB-type enhancers are involved in lipopolysaccharide-mediated transcriptional activation of the tumor necrosis factor α gene in primary macrophages," 1990, *J. Exp. Med.*, vol. 171, p. 35-47.

Schett, G., "Review: Immune cells and mediators of inflammatory arthritis," 2008, *Autoimmunity*, vol. 41, p. 224-229.

Su, B. et al. "Mitogen-activated protein kinase cascades and regulation of gene expression," 1996, *Current Opinion in Immunology*, vol. 8, p. 402-411.

Tracey, K. et al. "Anti-cachectin/TNF monoclonal antibodies prevent septic shock during lethal bacteraemia," 1987, *Nature*, vol. 330, p. 662-664.

Tracey, K. et al. "Tumor necrosis factor: a pleiotropic cytokine and therapeutic target," 1994, *Annu. Rev. Med.*, vol. 45, p. 491-503.

Trede, N. et al. "Transcriptional activation of the human TNG-α promoter by superantigen in human monocytic cells: role of NF-κB," 1995, *J. Immunol.*, vol. 155, p. 902-908.

Van Der Poll, T. et al. "Host-pathogen interactions in sepsis," 2008, *Lancet Infect Dis.*, vol. 8, p. 32-43.

Woodworth, C. at al., "Interleukin 1α and tumor necrosis factor α stimulate autocrine amphiregulin expression and proliferation of human papillomavirus-immortalized and carcinoma-derived cervical epithelial cells," 1995, *Proc. Natl. Acad. Sci.*, vol. 92, p. 2840-2844.

Zeigler-Heitbrock, H. et al. "Pyrrolidine dithiocarbamate inhibits NF-κB mobilization and TNF production in human monocytes," 1993, *J. Immunol.*, vol. 151, p. 6986-6993.

Fache, Fabienne et al., "Total synthesis of cimiracemate B and analogs," *Tetrahedron*, 2005, vol. 61, p. 5261-5266.

Plietker, Bernd, "The $RuO_4$-Catalyzed Ketohydroxylation, Part II: A Regio-, Chemo- and Stereoselectivity Study," *European Journal of Organic Chemistry*, 2005, p. 1919-1929.

\* cited by examiner

Compound A1

Compound A2

Cim A

COMPOUNDS AND USES THEREOF FOR TREATING INFLAMMATION AND MODULATING IMMUNE RESPONSES

CROSS-REFERENCE TO A RELATED APPLICATION

This application claims the benefit of U.S. provisional application Ser. No. 61/608,347, filed Mar. 8, 2012, which is incorporated herein by reference in its entirety.

BACKGROUND OF THE INVENTION

In response to injury, cancer, microbial invasion, and the like, humans mount inflammatory reactions to control the pathological condition and to initiate a repair process. During inflammation, various immune cells including T-lymphocytes, neutrophils and macrophages are recruited to the site of infection and produce cytokines to facilitate the immune response. Among these cytokines, tumor necrosis factor-α (TNF-α) is one of the major proinflammatory proteins to mediate the immune defense.

In addition to acute phase response, TNF-α has been shown to be involved in the progression of various chronic diseases including tumorigenesis and rheumatoid arthritis (RA). The dysregulation of TNF-α production was demonstrated to be involved in different stages of tumorigenesis including initiation of tumor growth[1], cell proliferation[2] and invasion[3]. For tumor cell proliferation, TNF-α upregulates specific growth factors to mediate the malignant growth. The cytokine promotes angiogenesis favoring growth of blood vessels to support the tumor migration, and thus plays a key role in tumor metastasis. For example, glioblastoma migration and induction of metalloproteinases are significantly enhanced in response to TNF-α effects[4].

Examples of chronic disease pathogenesis mediated by TNF-α include rheumatoid arthritis and inflammatory bowel diseases. Patients with rheumatoid arthritis have a low grade insidious inflammation in the synovial tissues. It is known that overproduction of TNF-α at the inflamed joint leads to slow destruction of the joint cartilage and surrounding bone.

During an acute phase of infection such as in the case of sepsis, uncontrolled production of TNF-α is well known to cause deleterious effects to the host. Sepsis is the second most common cause of death in non-coronary intensive care units and the tenth leading cause of death overall in high-income countries[5]. The clinical outcome of infection leading to sepsis is primarily associated with the excessive stimulation of the host immune cells, particularly monocytes or macrophages, by bacterial endotoxins (e.g., lipopolysaccharide [LPS])[6-8]. Macrophages overstimulated by LPS also produce high levels of mediators such as interleukin-1 (IL-1), IL-6, and TNF-α[9]. These mediators are implicated in the pathogenesis of sepsis and found to be contributing factors to the demise of the host. The development of novel therapies directed towards the inhibition of TNF-α production may help to aid in the treatment of these acute and chronic diseases described above.

Following exposure to pathogens and endotoxins, intracellular signaling pathways including specific kinases and transcription factors are activated to induce the expression of TNF-α. The involvement of mitogen-activated protein (MAP) kinases and the nuclear factor kappa B (NF-κB) in pathogen-induced TNF-α expression are well documented[10-12]. *Mycobacteria*, avian influenza and HIV-1 Tat protein are inducers of TNF-α through the MAP kinases[13-15].

There are three MAP kinase subtypes including extracellular signal-regulated kinase-1/2 (ERK 1/2), p38 MAP kinase and c-Jun N-terminal kinase (JNK)[16-20] known in humans. They transduce a variety of extracellular stimuli through a cascade of protein phosphorylations that lead to the activation of transcription factors such as NF-κB. The activation of NF-κB is crucial in production of cytokines including IL-6 and TNF-α[13-15]. The process occurs by the phosphorylation of I-κB at Ser32 and Ser36 via the I-κB kinase (IKK) signalosome complex followed by proteosomal degradation[21] and consequent dissociation of I-κB and NF-κB subunits[22]. The activated NF-κB is then translocated from the cytoplasm to the nucleus, where it binds to κB binding sites in the promoter region of responsive genes, leading to the initiation of transcription of pro-inflammatory mediators. Because inappropriate activation of NF-κB is associated with a wide range of human diseases[23], it has been considered as a plausible target for therapeutic intervention.

Currently, in the treatment for rheumatoid arthritis, psoriasis, psoriatic arthritis and ankylosing spondylitis, monoclonal TNF-α antibody plays an important role in the control of disease progression. Similarly, several randomized, double blind, placebo-controlled clinical trials had been performed in patients with Crohn's disease. The results of these clinical trials showed that the anti-TNF-α antibody (Infliximab) has beneficial effects to the patients[24].

Additionally, recent studies showed that inflammatory responses including TNF-α production may play an important role in the pathogenesis of cardiovascular diseases (CVD). It has been suggested that TNF-α may destabilize the atherogenesis and atherosclerotic plaques leading to their rupture, resulting in myocardial infraction or stroke in CVD patients.

During microbial infection, macrophages are activated to produce cytokines to mediate immune response. Depending on the invading microbe and its biological properties, the host immune system utilizes different sets of cytokines to combat the invading pathogen locally and systemically.

A good example is mycobacterial infection, in which the proinflammatory cytokines TNF-α plays a critical role in host survival by propagating inflammation to contain the microbes by the formation of granuloma[25]. The protective role of TNF-α in controlling mycobacterial growth is exemplified by the resurgence of tuberculosis in patients receiving anti-TNF-α antibody therapy[26].

Although the effects of proinflammatory cytokines are protective, their overproduction may have adverse effects to the host. In fact, uncontrolled induction of proinflammatory cytokine can lead to complications such as hypotension, organ failure and even death[27, 28]. Indeed, the overproduction of TNF-α in endotoxemia patients leads to serious deleterious symptoms. In chronic diseases such as rheumatoid arthritis, TNF-α overexpression is known to be the damaging factor and is associated with progressive joint destruction[29].

In recent years, immunotherapeutics have been developed which aim at the neutralization of TNF-α and suppression of its undesirable proinflammatory effects. These include soluble TNF-α receptor (Enbrel) and anti-TNF-α antibody (Infliximab). Despite their novelty and efficacy in the arrest of disease progression, they are very expensive therapeutic regimens. Additionally, non-steroid anti-inflammatory drugs (NSAIDs) including aspirin, ibuprofen, and indomethacin are well-known in ameliorating acute and chronic pain associated with inflammatory diseases such as rheumatoid arthritis and inflammatory bowel disease. However, they are not effective in the treatment of advanced stages of rheumatoid arthritis and related autoimmune diseases. Also, these drugs are associated with severe adverse effects including gastrointestinal irritation, severe bleeding, and bone marrow suppression. Accordingly, therapeutics for treating inflammatory diseases and immune disorders are needed.

BRIEF SUMMARY

The present invention provides compounds, and compositions comprising these compounds, which have immunomodulatory activity and/or anti-inflammatory activity.

In one embodiment, the present invention provides compounds represented by formula (I), and salts thereof:

wherein $R_1$-$R_5$ and $R_{10}$-$R_{14}$ are, independently, H, OH, a straight or branched chain $C_1$ to $C_6$ alkyl group (e.g., a methyl, ethyl, n-propyl, isopropyl, cyclopropyl, n-butyl, isobutyl, s-butyl or t-butyl group), a $C_2$ to $C_6$ alkenyl group, a $C_2$ to $C_6$ alkynyl group, a $C_1$ to $C_6$ alkoxy group, halo, amino, alkylamino, acyl, cyano, nitro, haloalkyl, carbonyl, trifluoromethyl, ester, —COCH$_3$, or —COOH;

$R_6$ and $R_7$ are, independently, H, a straight or branched chain $C_1$ to $C_6$ alkyl group, halo, amino, alkylamino, acyl, or —COOH;

$R_8$ and $R_9$ are, independently, H, OH, a straight or branched chain $C_1$ to $C_6$ alkyl group, alkoxy, halo, amino, alkylamino, acyl, or —COOH;

A is an oxygen, carbon, sulfur, or nitrogen atom; and the alkyl, alkenyl, alkynyl, alkylamino, and alkoxy groups can be substituted or unsubstituted.

In certain embodiments, the present invention provides substantially compounds represented by formula (I), with the proviso that at least one of the following is true:

a) $R_1$ is selected from H, OH, a straight or branched chain $C_1$ to $C_6$ alkyl group, a $C_2$ to $C_6$ alkenyl group, a $C_2$ to $C_6$ alkynyl group, a $C_1$ to $C_6$ alkoxy group, halo, amino, alkylamino, acyl, cyano, nitro, haloalkyl, carbonyl, trifluoromethyl, ester, —COCH$_3$, or —COOH;

b) at least one of $R_2$, $R_{12}$ and $R_{13}$ is selected from H, a straight or branched chain $C_1$ to $C_6$ alkyl group, a $C_2$ to $C_6$ alkenyl group, a $C_2$ to $C_6$ alkynyl group, halo, amino, alkylamino, acyl, cyano, nitro, haloalkyl, carbonyl, trifluoromethyl, ester, —COCH$_3$, or —COOH;

c) A is a carbon, oxygen, sulfur, or nitrogen atom; and d) at least one of $R_6$ and $R_7$ is not H.

In one specific embodiment, the present invention provides Compound A1, having the following structure:

(Compound A1)

In another specific embodiment, the present invention provides Compound A2, having the following structure:

(Compound A2)

Advantageously, in one embodiment, the compounds of the present invention can inhibit LPS-induced TNF-α production.

The present invention is also directed to pharmaceutical compositions comprising a pharmaceutically acceptable carrier and a compound of the invention. In a preferred embodiment, the composition contains a compound of the invention as the active ingredient.

The present invention is also directed to methods of use of the compounds or compositions comprising them, for the inhibition of inflammation in animals, preferably mammals, including humans. The present invention is also directed to methods of use of said compounds or compositions comprising said compounds for the modulation of immune activity in animals, preferably mammals, including humans.

BRIEF DESCRIPTION OF THE DRAWINGS

FIGS. 2 (A-C) show the inhibition of LPS-induced TNF-α production by Compound A1, Compound A2 and Cim A. PBMac cells are incubated with (A) 25 and 50 ug/ml A1 or (B) 25 and 50 ug/ml A2 or (C) 25 and 50 ug/ml Cim A for 18 h prior to the addition of 10 ng/ml LPS for another 24 h. The culture supernatants are collected and assayed for TNF-α production by enzyme-linked immunosorbent assay (ELISA). The results shown are the mean values±standard derivation (S.D.) of at least three independent experiments, with cells obtained from different donors. * $P<0.05$, ** $P<0.01$ compared with the control.

DETAILED DESCRIPTION

The present invention provides compounds having useful immunomodulatory and/or anti-inflammatory activities. The present invention further provides compositions comprising these compounds as well as methods for the use in treating inflammatory and immune conditions in a subject.

Compounds

In one aspect, the present invention provides compounds that have potent anti-inflammatory and immunomodulatory effects.-

In one embodiment, the present invention provides compounds represented by formula (I), and salts thereof:

wherein $R_1$-$R_5$ and $R_{10}$-$R_{14}$ are, independently, H, OH, a straight or branched chain $C_1$ to $C_6$ alkyl group (e.g., a methyl, ethyl, n-propyl, isopropyl, cyclopropyl, n-butyl, isobutyl, s-butyl or t-butyl group), a $C_2$ to $C_6$ alkenyl group, a $C_2$ to $C_6$ alkynyl group, a $C_1$ to $C_6$ alkoxy group, halo, amino, alkylamino, acyl, cyano, nitro, haloalkyl, carbonyl, trifluoromethyl, ester, —$COCH_3$, or —COOH;

$R_6$ and $R_7$ are, independently, H, a straight or branched chain $C_1$ to $C_6$ alkyl group, halo, amino, alkylamino, acyl, or —COOH;

$R_8$ and $R_9$ are, independently, H, OH, a straight or branched chain $C_1$ to $C_6$ alkyl group, alkoxy, halo, amino, alkylamino, acyl, or —COOH;

A is an oxygen, carbon, sulfur, or nitrogen atom; and the alkyl, alkenyl, alkynyl, alkylamino, and alkoxy groups can be substituted or unsubstituted.

In certain embodiments, the present invention provides substantially compounds represented by formula (I), with the proviso of at least one of the following:

a) $R_1$ is selected from H, OH, a straight or branched chain $C_1$ to $C_6$ alkyl group, a $C_2$ to $C_6$ alkenyl group, a $C_2$ to $C_6$ alkynyl group, a $C_1$ to $C_6$ alkoxy group, halo, amino, alkylamino, acyl, cyano, nitro, haloalkyl, carbonyl, trifluoromethyl, ester, —$COCH_3$, or —COOH;

b) at least one of $R_2$, $R_{12}$ and $R_{13}$ is selected from H, a straight or branched chain $C_1$ to $C_6$ alkyl group, a $C_2$ to $C_6$ alkenyl group, a $C_2$ to $C_6$ alkynyl group, halo, amino, alkylamino, acyl, cyano, nitro, haloalkyl, carbonyl, trifluoromethyl, ester, —$COCH_3$, or —COOH;

c) A is a carbon, oxygen, sulfur, or nitrogen atom; and d) at least one of $R_6$ and $R_7$ is not H. In certain embodiments, the alkyl groups of $R_1$-$R_{14}$ are, independently, a $C_1$ to $C_4$ alkyl, a $C_1$ to $C_3$ alkyl, an ethyl group, or a methyl group, all of which can be optionally substituted. In certain embodiments, at least one of $R_1$-$R_{14}$ is selected from H, OH, $OCH_3$, or $CH_3$.

In one embodiment, A is an oxygen atom. In one embodiment, one or more of $R_6$-$R_9$ are H.

In one embodiment, at least one of $R_1$, $R_2$ and $R_{13}$ is OH. In another embodiment, both of $R_1$ and $R_2$ are OH. In one embodiment, $R_1$ is $OCH_3$. In one embodiment, $R_2$ is H. In another embodiment, either or both of $R_{12}$ and $R_{13}$ are OH.

In one embodiment, one or more of $R_1$-$R_{14}$ are not H. In another embodiment, one or more of $R_3$-$R_{14}$ are not H.

In one specific embodiment, the present invention provides Compound A1, having the following structure:

(Compound A1)

In another specific embodiment, the present invention provides Compound A2, having the following structure:

(Compound A2)

Advantageously, the compounds of the present invention have anti-inflammatory and immunomodulatory activity. In certain embodiments, the compounds of the present invention inhibit TNF-α production. Since overproduction of TNF-α is toxic and can result in severe complications, limiting this overwhelming inflammatory response can be beneficial to patients in clinical management.

In addition, the compounds of the present invention abrogate MAP kinase and/or NF-κB activation. TNF-α, MAP kinase and NF-κB are mediators that play a key role in production of cytokine and regulation of a range of immune responses. Therefore, the compounds of the present invention can also be used to regulate the downstream effectors of TNF-α.

In addition, the compounds of the present invention inhibit 5-lipoxygenase (5-LOX) activity and block the biosynthesis of leukotrienes such as $LTB_4$. It has been reported that 5-LOX inhibition blocks biosynthesis and activity of a wide range of proinflammatory mediators, including lipoxins, leukotrienes, prostaglandins, and thromboxanes. Particularly, it is well documented that inhibition of 5-LOX blocks biosynthesis of leukotrienes. Therefore, the present compounds are useful for preventing, reversing or alleviating pathological conditions induced by leukotrienes.

As exemplified in the present invention, Compound A1 and Compound A2 potently reduce LPS-induced TNF-α production.

The term "alkyl," as used herein, refers to a linear or branched saturated monovalent radical that contains carbon and hydrogen. In some embodiments, alkyl groups contain from one to about eight carbon atoms, and may include hydrocarbon radicals of one to four or one to three carbon atoms which may be linear. Representative examples of alkyl groups include, but are not limited to, methyl, ethyl, propyl, 2-propyl, n-butyl, iso-butyl, tert-butyl, and pentyl.

The term "alkenyl" or "alkenylene," respectively, refers to a monovalent or divalent hydrocarbyl radical which has at least one double bond. The alkenyl or alkenylene group may be cyclic, branched acyclic or straight acyclic. In some embodiments, the alkenyl or alkenylene group contains only one double bond. In other embodiments, the alkenyl or alkenylene group contains two or more double bonds. In further embodiments, the alkenyl or alkenylene group can be a lower alkenyl or alkenylene containing from two to eight carbon atoms in the principal chain, as exemplified by ethenyl, propenyl, isopropenyl, butenyl, isobutenyl, hexenyl, and the like.

The term "alkynyl" or "alkynylene," respectively, refers to a monovalent or divalent hydrocarbyl radical that has at least a triple bond. In some embodiments, the alkynyl or alkynylene group contains only one triple bond. In other embodiments, the alkynyl or alkynylene group contains two or more triple bonds. In further embodiments, the alkynyl or alkynylene group can be a lower alkynyl or alkynylene containing from two to eight carbon atoms in the principal chain, as exemplified by ethynyl, propynyl, isopropynyl, butynyl, isobutynyl, hexynyl, and the like.

The term "hydrocarbon" or "hydrocarbyl" refers to organic compounds or radicals consisting exclusively of the elements carbon and hydrogen. Hydrocarbyl includes alkyl, alkenyl, and alkynyl moieties.

The term "acyl" means a radical —C(O)R wherein R is hydrogen, alkyl or cycloalkyl, or heterocycloalkyl. In one embodiment, the R group of the radical —C(O)R is a $C_1$ to $C_4$ alkyl. Examples of acyl groups include, but are not limited to, formyl, acetyl, and ethylcarbonyl.

The term "halo" means fluoro, chloro, bromo, and iodo.

The term "hydroxy" means the radical —OH.

The term "substituted," as used herein, refers to that at least one hydrogen atom of a compound or chemical moiety is replaced with a second chemical moiety. Non-limiting examples of substituents are those found in the exemplary compounds and embodiments disclosed herein, as well as halogen; alkyl; alkenyl; alkynyl; hydroxy; alkoxyl; amino; haloalkyl (e.g., trifluoromethyl); and —COOH. All chemical groups disclosed herein can be substituted, unless it is specified otherwise. For example, "substituted" alkyl, alkenyl, or alkynyl moieties described herein are moieties that are substituted with a second chemical moiety such as a hydrocarbyl moiety, halo, alkoxy, and —COOH. Substituted alkyl groups include, but are not limited to, haloalkyl, hydroxyalkyl, carboxylalkyl, and aminoalkyl.

The term "haloalkyl" means alkyl substituted with one or more same or different halo atoms. Representative examples of haloalkyl groups include, but are not limited to, —$CH_2Cl$, —$CH_2Br$, —$CF_3$, —$CH_2CH_2Cl$, and —$CH_2CCl_3$.

The term "amino," as used herein, refers to —$NH_2$.

The term "alkylamino" means a radical —NHR or —$NR_2$ where each R is independently an alkyl group. In certain embodiments, the alkyl group of alkylamino is a $C_1$ to $C_4$ alkyl. Representative examples of alkylamino groups include, but are not limited to, methylamino, (1-methylethyl) amino, methylamino, dimethylamino, methylethylamino, and di(1-methylethyl)amino.

The term "hydroxyalkyl" means an alkyl radical as defined herein, substituted with one or more, preferably one, two or three hydroxy groups. In certain embodiments, hydroxyalkyl is a $C_1$ to $C_6$ alkyl, or preferably a $C_1$ to $C_4$ alkyl, substituted with one or more hydroxy groups. Representative examples of hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl, and 1-(hydroxymethyl)2-hydroxyethyl.

The term "alkoxy," as used herein, refers the radical —$OR_x$, wherein Rx is a $C_1$ to $C_6$ alkyl group. In one embodiment, Rx is a $C_1$ to $C_4$ alkyl group. Exemplary alkoxy groups include, but are not limited to, methoxy, ethoxy, and propoxy.

In certain embodiments, the present invention provides substantially pure compounds represented by formula (I). The term "substantially pure," as used herein, refers to more than 99% pure.

The compounds of the present invention can be isolated from plants or can be synthesized. As used herein, "isolated" refers to compounds that have been removed from any environment in which they may exist in nature. For example, an isolated Compound X would not refer to the Compound X as it exists in plants from which Compound X can be isolated. In preferred embodiments, the compounds of the present invention are at least 75% pure, preferably at least 90% pure, more preferably are more than 95% pure, and most preferably are more than 99% pure (substantially pure).

The present invention further embodies stereoisomers of the compounds of formula (I). The term "stereoisomer" encompasses all enantiomerically/stereomerically pure and enantiomerically/stereomerically enriched compounds disclosed herein.

In one embodiment, the present invention pertains to enantiomeric forms of the compounds of formula (I). The enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least about 99% enantiomeric excess.

In certain embodiments, the compounds of formula (I) do not include any of the compounds disclosed in International Application No.: PCT/IB2009/055970 and International Application No.: PCT/IB2011/002582.

In one specific embodiment, the compounds of formula (I) do not include Cimiracemate A (Cim A), having the following structure:

In certain embodiments, the compounds of formula (I) do not include the following compounds:
1) the compounds of formula (X)

wherein $R_1$ is H, $R_2$ is $CH_3$, and $R_3$ is H;
wherein $R_1$ is $CH_3$, $R_2$ is H, and $R_3$ is H;
wherein $R_1$ is $CH_3$, $R_2$ is H, and $R_3$ is $OCH_3$;
wherein $R_1$ is H, $R_2$ is $CH_3$, and $R_3$ is $OCH_3$; or
wherein $R_1$ is H, $R_2$ is H, $R_3$ is H;
2) the compounds of formula (XI)

wherein $R_1$ is $OCH_3$, $R_2$ is OH, $R_3$ is $OCH_3$, and $R_4$ is OH;
wherein $R_1$ is H, $R_2$ is OH, $R_3$ is $OCH_3$, and $R_4$ is OH;
wherein $R_1$-$R_3$ are, independently, $OCH_3$, and $R_4$ is OH;
wherein $R_1$-$R_2$ are $OCH_3$, and $R_3$-$R_4$ OH; or
wherein $R_1$-$R_2$ are H, $R_3$ is $OCH_3$, and $R_4$ is OH; and
3) the compound of formula (XII)

wherein $R_1$ is H, $R_2$ is $CH_3$.

In certain embodiments, the compounds of formula (I) do not include the compounds disclosed in the following references: He et al., Cimicifuga species identification by high performance liquid chromatography-photodiode array/mas spectrometric/evaporative light scattering detection for quality control of black cohosh products, *Journal of Chromatography A,* 1112 (2006) 241-254; Japanese Patent Application Publication No. JP2005-029571; Mizushina et al., Petasiphenol: a DNA polymerase λ inhibitor, *Biochemistry* (2002), 41 14463-14471; Burdette et al., Black Cohosh (*Cimicifuga Racemosa* L.) protects against menadione-induced DNA damage through scavenging of reactive oxygen species: bioassay-directed isolation and characterization of active principles, *J. Agric. Food Chem.* (2002), 50, 7022-7028; Fache et al. Total synthesis of cimiracemate B and analogs, *Tetrahedron* 61 (2005) 5261-5266; Mizushina et al., Some anti-chronic inflammatory compounds are DNA polymerase λ inhibitors, *Biochemistry Phamacology* 66 (2003), 1935-1944; Takeuchi et al., Structural relationship of curcumin derivatives binding to the BRCT domain of human DNA polymerase λ, *Genes to Cells* (2006) 11, 223-235; and *Phytochemistry* (2002) Vol. 61 No. 4 pages 409-413.

The compounds of the present invention can be prepared using techniques known in the art, including the techniques described in International Application No.: PCT/IB2009/055970 and International Application No.: PCT/IB2011/002582, and publications including He et al., *Cimicifuga* species identification by high performance liquid chromatography-photodiode array/mas spectrometric/evaporative light scattering detection for quality control of black cohosh products, *Journal of Chromatography A,* 1112 (2006) 241-254; Japanese Patent Application Publication No. JP2005-029571; Mizushina et al., Petasiphenol: a DNA polymerase λ, inhibitor, *Biochemistry* (2002), 41 14463-14471; Burdette et al., Black Cohosh (*Cimicifuga Racemosa* L.) protects against menadione-induced DNA damage through scavenging of reactive oxygen species: bioassay-directed isolation and characterization of active principles, *J. Agric. Food Chem.* (2002), 50, 7022-7028; Fache et al. Total synthesis of cimiracemate B and analogs, *Tetrahedron* 61 (2005) 5261-5266; Mizushina et al., Some anti-chronic inflammatory compounds are DNA polymerase λ inhibitors, *Biochemistry Phamacology* 66 (2003), 1935-1944; Takeuchi et al., Structural relationship of curcumin derivatives binding to the BRCT domain of human DNA polymerase λ, *Genes to Cells* (2006) 11, 223-235; and *Phytochemistry* (2002) Vol. 61 No. 4 pages 409-413, all of which are incorporated by reference in their entireties.

Treatment of Inflammatory Diseases and/or Immune Disorders

The present invention provides uses of compounds of the present invention as well as compositions comprising these compounds for treatment of inflammatory diseases and immune disorders. In certain embodiments, the present invention provides treatment of inflammation, allergenic reactions, diseases associated with cell proliferation, neoangiogenesis, and cardiovascular diseases. In one specific embodiment, the compounds of the present invention can be used to treat arthritis.

In one embodiment, the present invention provides a method for treating inflammatory diseases and immune disorders, wherein the method comprises administering, to a subject in need of such treatment, an effective amount of a compound of formula (I), or a prodrug or metabolite thereof.

In preferred embodiment, the present invention pertains to uses of Compounds A1 and A2 for treatment of inflammation and immune disorders.

The term "treatment" or any grammatical variation thereof (e.g., treat, treating, and treatment etc.), as used herein, includes but is not limited to, alleviating or ameliorating a symptom of a disease or condition, and/or reducing the severity of a disease or condition.

The term "effective amount," as used herein, refers to an amount that is capable of treating or ameliorating a disease or condition or otherwise capable of producing an intended therapeutic effect.

The term "subject" or "patient," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; domesticated animals such as dogs, cats; live stocks such as horses, cattle, pigs, sheep, goats, chickens; and other animals such as mice, rats, guinea pigs, and hamsters.

In one embodiment, the subject in need of treatment is diagnosed with an inflammatory disease or immune disorder that can be treated in accordance with the present invention. In one embodiment, the present invention comprises: diagnosing whether the subject has an inflammatory disease or immune disorder that can be treated in accordance with the present invention.

The compounds and pharmaceutical compositions of the present invention can be used in the treatment or amelioration of inflammatory symptoms in any disease, condition or disorder where immune and/or inflammation suppression is beneficial. Inflammatory diseases, conditions or disorders in which the compounds and compositions of the present invention can be used to inhibit unwanted immune reactions and inflammation include, but are not limited to, arthritis, including but not limited to rheumatoid arthritis, and other diseases, conditions or disorders of the joints or musculoskeletal system in which immune and/or inflammation suppression is beneficial.

Moreover, the compounds and compositions are also useful to treat or ameliorate inflammation associated with atherosclerosis; arteriosclerosis; atherosclerotic heart disease; reperfusion injury; cardiac arrest; myocardial infarction; vascular inflammatory disorders including cerebro-vascular disease (stroke); respiratory distress syndrome and other cardiopulmonary diseases, conditions or disorders where immune and/or inflammation suppression would be beneficial.

In addition, the compounds and compositions are also useful to treat or ameliorate inflammation associated with peptic ulcer; ulcerative colitis, Crohn's Disease, irritable bowel syndrome, other inflammatory bowel conditions, and other diseases, conditions or disorders of the gastrointestinal tract where immune inflammation suppression would be beneficial; hepatic fibrosis; liver cirrhosis and other hepatic diseases, conditions or disorders where immune and/or inflammation suppression would be beneficial; thyroiditis and other glandular diseases, conditions or disorders where immune and/or inflammation suppression would be beneficial; glomerulonephritis and other renal and urologic diseases, conditions or disorders where immune and/or inflammation suppression would be beneficial.

In addition, the compounds and compositions are also useful to treat or ameliorate inflammation associated with post-traumatic inflammation; septic shock; infectious diseases where immune and/or inflammation suppression would be beneficial; inflammatory complications and side effects of surgery where immune and/or inflammation suppression would be beneficial; bone marrow transplantation and other transplantation complications and/or side effects where immune and/or inflammation suppression would be beneficial; inflammatory and/or immune complications and side effects of gene therapy, e.g., due to infection with a viral carrier; and inflammation associated with acquired immune deficiency syndrome (AIDS).

In certain embodiments, the compounds and pharmaceutical compositions of the present invention are useful to treat or ameliorate asthma and asthma-associated diseases, such as for example, exercise-induced asthma, rhinitis, chronic obstructive pulmonary disease, interstitial lung disease, chronic urticaria, atopic dermatitis, allergic fungal diseases, nasal polyposis, and paranasal sinus disease.

In addition, the compounds and pharmaceutical compositions of the present invention are useful to treat or ameliorate non-asthma-related diseases, including migraine, respiratory syncytial virus postbronchiolitis, systemic mastocytosis, cystic fibrosis, pancreatitis, vulvovaginal candidiasis, cancer, atherosclerosis, eosinophils cystitis, otitis media, capsular contracture, and eosinophilic gastrointestinal disorders.

In addition, the compounds and pharmaceutical compositions of the present invention are useful to treat or ameliorate diseases, including cerebrovascular and cardiovascular diseases such as myocardial infarction, acute myocardial infarction, stroke, atherosclerosis, thrombosis, coronary angioplasty, aortic aneurysms, vascular inflammation, intimal hyperplasia, hyperlipidemia-dependent aortic aneurysm; cystic fibrosis lung diseases; sleep-disorder breathing, obstructive sleep apnea (OSA); and chronic obstructive pulmonary disease (COPD).

In addition, the compounds and pharmaceutical compositions of the present invention are useful to treat or ameliorate diseases, including pulmonary disorders including diseases such as asthma, chronic bronchitis, and related obstructive airway diseases; allergies and allergic reactions such as allergic rhinitis, contact dermatitis, allergic conjunctivitis, and the like; inflammation such as arthritis or inflammatory bowel disease; pain; skin disorders such as psoriasis, atopic eczema, and the like; cardiovascular disorders such as angina, myocardial ischemia, hypertension, platelet aggregation and the like; renal insufficiency arising from ischemia induced by immunological or chemical (cyclosporin) etiology; migraine or cluster headache; ocular conditions such as uveitis; hepatitis resulting from chemical, immunological or infectious stimuli; trauma or shock states such as burn injuries, endotoxemia and the like; allograft rejection; chronic lung diseases such as cystic fibrosis, bronchitis and other small and large-airway diseases; and cholecystitis.

Further, the compounds and compositions are also useful to inhibit macrophage or T cell associated aspects of an immune response that are not associated with inflammation. The compounds and compositions are able to inhibit macrophage or T cell activities including, but not limited to, macrophage antigen-presenting activity, macrophage cytokine production, T cell cytokine production, T cell adhesion activity, T cell proliferation, etc. Thus, the peptides, peptide derivatives and compositions are useful to suppress or inhibit a humoral and/or cellular immune response.

The compounds and compositions are also useful to treat or ameliorate monocyte and leukocyte proliferative diseases, e.g., leukemia, by reducing the amount of monocytes and lymphocytes.

The compounds and pharmaceutical compositions of the invention are further useful for the prevention and/or treatment of graft rejection in cases of transplantation of natural or artificial cells, tissue and organs, such as cornea, bone marrow, organs, lenses, pacemakers, natural and artificial skin tissue, and the like.

The compounds and compositions are also useful to treat or ameliorate inflammation associated with otitis and other otorhinolaryngological diseases, conditions or disorders where immune and/or inflammation suppression would be beneficial; dermatitis and other dermal diseases, conditions or disorders where immune and/or inflammation suppression would be beneficial; periodontal diseases and other dental diseases, conditions or disorders where immune and/or inflammation suppression would be beneficial.

In addition, the compounds and compositions are also useful to treat or ameliorate inflammation associated with posterior uveitis; intermediate uveitis; anterior uveitis; conjunctivitis; chorioretinitis; uveoretinitis; optic neuritis; intraocular inflammation, such as retinitis and cystoid macular edema; sympathetic ophthalmia; scleritis; retinitis pigmentosa; immune and inflammatory components of degenerative fondus disease; inflammatory components of ocular trauma; ocular inflammation caused by infection; proliferative vitreoretinopathies; acute ischemic optic neuropathy; excessive scarring, for example, following glaucoma filtration operation; immune and/or inflammation reaction against ocular implants and other immune and inflammatory-related ophthalmic diseases, conditions or disorders where immune and/or inflammation suppression would be beneficial.

Moreover, the compounds and compositions are also useful to treat or ameliorate inflammation associated with autoimmune diseases and conditions or disorders where, both in the central nervous system (CNS) and in any other organ, immune and/or inflammation suppression would be beneficial; Parkinson's disease; complications and/or side effects from treatment of Parkinson's disease; AIDS-related dementia complex (HIV-related encephalopathy); Devic's disease; Sydenham chorea; Alzheimer's disease and other degenerative diseases, conditions or disorders of the central nervous system where immune and/or inflammation suppression would be beneficial; inflammatory components of strokes; post-polio syndrome; immune and inflammatory components of psychiatric disorders; myelitis; encephalitis; subacute sclerosing panencephalitis; encephalomyelitis; acute neuropathy; subacute neuropathy; chronic neuropathy; Guillain-Barre syndrome; Sydenham chorea; myasthenia gravis; pseudotumor cerebri; Down's Syndrome; Huntington's disease; amyotrophic lateral sclerosis; inflammatory components of central nervous system (CNS) compression or CNS trauma or cerebrovascular accidents (stroke) or infections or hypoxia-ischemia of the CNS; inflammatory components of muscular atrophies and dystrophies; and immune and inflammatory related diseases, conditions or disorders of the central and peripheral nervous systems where immune and/or inflammation suppression would be beneficial.

In yet another embodiment, the compounds and compositions of the invention are useful to restore immune privilege at an immune privileged site which has lost its immune privilege such as brain, eye and testis.

Therapeutic Compositions and Formulations

The present invention also provides for therapeutic or pharmaceutical compositions comprising a compound of the invention in a form that can be combined with a pharmaceutically acceptable carrier. In this context, the compound may be, for example, isolated or substantially pure. The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions. Particularly preferred pharmaceutical carriers for treatment of or amelioration of inflammation in the central nervous system are carriers that can penetrate the blood/brain barrier. As used herein carriers do not include the natural plant material as it exists in nature.

The present invention also pertains to uses of prodrugs and metabolites of the compounds. The term "prodrug," as used herein, refers to a metabolic precursor of a compound of the present invention or pharmaceutically acceptable form thereof. In general, a prodrug comprises a functional derivative of a compound, which may be inactive when administered to a subject, but is readily convertible in vivo into an active metabolite compound. Conventional procedures for the selection and preparation of suitable prodrug derivatives are described, for example, in "Design of Prodrugs", ed. H. Bundgaard, Elsevier, 1985. Preferably, a prodrug of the present invention enhances desirable qualities of the compound of the present invention including, but not limited to, solubility, bioavailability, and stability. Hence, the compounds employed in the present methods may, if desired, be delivered in a prodrug form. Prodrugs of the compounds employed in the present invention may be prepared by modifying functional groups present in the compound such that the modifications are cleaved, either in routine manipulation or in vivo, to the parent compound.

The term "metabolite," refers to a pharmacologically active product, including for example, an active intermediate or an ultimate product, produced through in vivo metabolism of a compound of the present invention in a subject. A metabolite may result, for example, from the anabolic and/or catabolic processes of the administered compound in a subject, including but not limited to, the oxidation, reduction, hydrolysis, amidation, deamidation, esterification, deesterification, enzymatic cleavage, and the like.

Metabolites are typically identified by preparing a radiolabelled (e.g., $^{14}C$ or $^3H$) isotope of a compound of the present invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to about 30 hours), and isolating its conversion products from the urine, blood or other biological samples. These products are easily isolated since they are labeled (others are isolated by the use of antibodies capable of binding epitopes surviving in the metabolite). The structure of metabolites can be determined in conventional fashion, e.g., by MS, LC/MS or NMR analysis. In general, analysis of metabolites is performed according to techniques well known to those skilled in the art of drug metabolism studies.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

In one embodiment, the composition is formulated in accordance with routine procedures as a pharmaceutical composition adapted for local injection administration to human beings. Typically, compositions for local injection administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The present invention also provides for the modification of the compound such that it is more stable once administered to a subject, i.e., once administered it has a longer time period of effectiveness as compared to the unmodified compound. Such modifications are well known to those of skill in the art, e.g., microencapsulation, etc. The amount of the therapeutic or pharmaceutical composition of the invention which is effective in the treatment of a particular disease, condition or disorder will depend on the nature of the disease, condition or disorder and can be determined by standard clinical techniques. In general, the dosage ranges from about 0.001 mg/kg to about 500 mg/kg.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems. For example, in order to obtain an effective ng/kg dose for humans based on data generated from rat studies, the effective mg/kg dosage in rats is divided by six.

For instance, suitable unit dosages may be between about 0.01 to about 500 mg, about 0.01 to about 300 mg, about 0.01 to about 200 mg, about 0.01 to about 100 mg, about 0.01 to about 50 mg, about 0.01 to about 30 mg, about 0.01 to about 20 mg, about 0.01 to about 10 mg, about 0.01 to about 5 mg, about 0.01 to about 3 mg, about, 0.01 to about 1 mg, or about 0.01 to about 0.5 mg. Such a unit dose may be administered more than once a day, e.g. two or three times a day.

The invention also provides a pharmaceutical pack or kit comprising one or more containers filled with one or more of the ingredients, e.g., compound, carrier, of the pharmaceutical compositions of the invention.

The compounds of the present invention can also be formulated consistent with traditional Chinese medicine practices. The composition and dosage of the formulation that are effective in the treatment of a particular disease, condition or disorder will depend on the nature of the disease, condition or disorder by standard clinical techniques.

The traditional Chinese medicine in prescription amounts can be readily made into any form of drug, suitable for administering to humans or animals. Suitable forms include, for example, tinctures, decoctions, and dry extracts. These can be taken orally, applied through venous injection or mucous membranes. The active ingredient can also be fog ululated into capsules, granules, powder, pallets, pastille, suppositories, oral solutions, pasteurized gastroenteric suspension injections, small or large amounts of injection, frozen powder injections, pasteurized powder injections and the like. All of the above-mentioned methods are known to people skilled in the art, described in books and commonly used by practitioners of herbal medicine.

In preferred embodiments, the compounds of the present invention are prepared as discrete units such as granules (e.g., wet granules, dry granules); capsules, cachets or tablets, each containing a predetermined amount of the active ingredient.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80%, or about 30% to about 70% active ingredient (w/w).

A tincture is prepared by suspending herbs in a solution of alcohol, such as, for example, wine or liquor. After a period of suspension, the liquid (the alcohol solution) may be administered for example, two or three times a day, one teaspoon each time.

A decoction is a common form of herbal preparation. It is traditionally prepared in a clay pot, but can also be prepared in glass, enamel or stainless steel containers. The formulation can be soaked for a period of time in water and then brought to a boil and simmered until the amount of water is reduced by, for example, half.

An extract is a concentrated preparation of the essential constituents of a medicinal herb. Typically, the essential constituents are extracted from the herbs by suspending the herbs in an appropriate choice of solvent, typically, water, ethanol/water mixture, methanol, butanol, iso-butanol, acetone, hexane, petroleum ether or other organic solvents. The extracting process may be further facilitated by means of maceration, percolation, repercolation, counter-current extraction, turbo-extraction, or by carbon-dioxide hypercritical (temperature/pressure) extraction. After filtration to rid of herb debris, the extracting solution may be further evaporated and thus concentrated to yield a soft extract (extractum spissum) and/or eventually a dried extract, extracum siccum, by means of spray drying, vacuum oven drying, fluid-bed drying or freeze-drying. The soft extract or dried extract may be further dissolved in a suitable liquid to a desired concentration for administering or processed into a form such as pills, capsules, injections, etc.

Following is an example that illustrates procedures and embodiments for practicing the invention. The example should not be construed as limiting. All percentages are by weight and all solvent mixture proportions are by volume unless otherwise noted.

Materials and Methods

Chemicals

Endotoxin (lipopolysachamide, LPS) from *E. coli* was purchased from Sigma and used as an inducer of TNF-α expression. Dexamethasone (Sigma) was used as a control drug to inhibit the LPS induction of TNF-α.

Cell Culture and Primary Blood Macrophage Isolation

Human peripheral blood monocytic cells (PBMC) were isolated from the buffy coat of healthy donor blood supplied by Hong Kong Red Cross by Ficoll-Paque (Amersham Pharmacia Biotech, Piscataway, N.J.) density gradient centrifugation as described in our previous reports. In brief, the buffy coat was spun at 3000 rotations per min (rpm) for 15 min to separate the blood cells and the plasma. The heat inactivated serum was filtered for future use.

The cell layer was diluted with phosphate buffered saline (PBS) in a ratio of 1:1. The diluted cells were overlaid on Ficoll-Paque slowly and centrifuged at 2300 rpm for 20 min for separation of mononuclear cells from erythrocytes. The mononuclear cell layer was removed and washed with RPMI 1640 medium until the supernatant was clear.

The cells were finally resuspended in RPMI 1640 medium supplemented with 5% autologous serum and cultured for 1 hr. The non-adherent cells were removed afterwards and the remaining adherent cells were further incubated for another 24 hr at 37° C. in 5% carbon dioxide ($CO_2$).

The adherent monocytic cells were detached and seeded onto tissue culture plates and incubated for another 7-14 days in order to differentiate the primary blood monocytic cells to primary blood macrophages (PBMac).

Enzyme-Linked ImmunoSorbent Assay (ELISA)

Culture supernatants of the LPS-treated PBMac, with or without pretreatment of Cim A, Compound A1 or Compound A2, were collected at different time intervals and stored at −70° C. The levels of the secreted TNF-α were measured by ELISA kits specific for the cytokine (R&D system, Minneapolis, Minn.).

EXAMPLE 1

Figure 1:
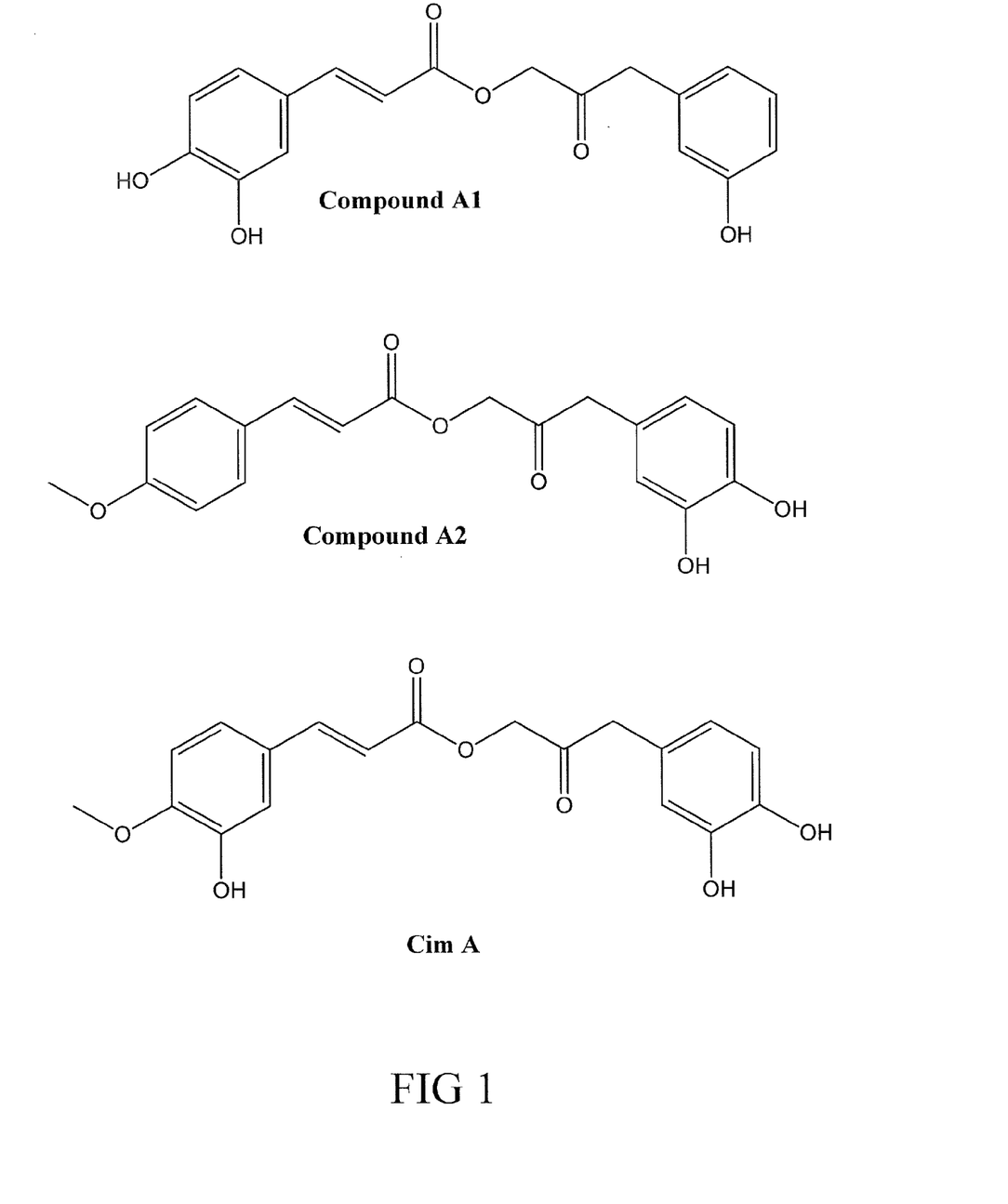
FIG. 1 shows the chemical structures of Compound A1, Compound A2, and Cimiracemate A (Cim A).
Figure 2A:
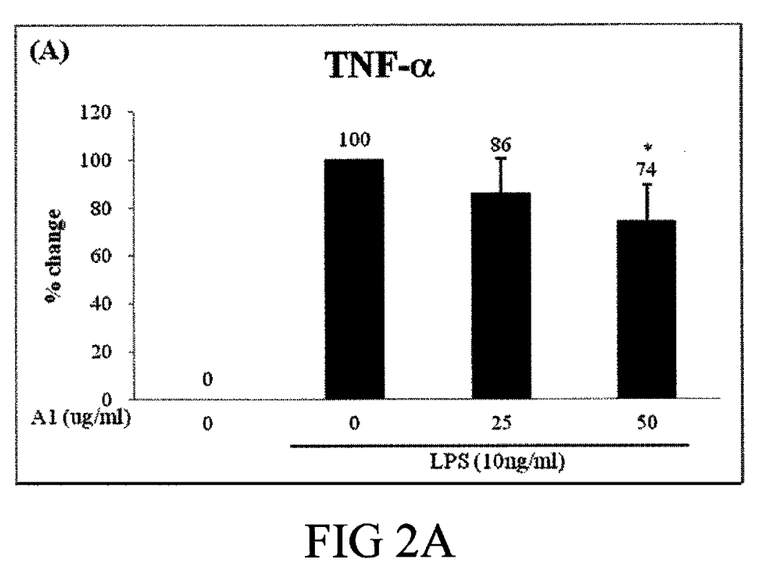
Figure 2B:
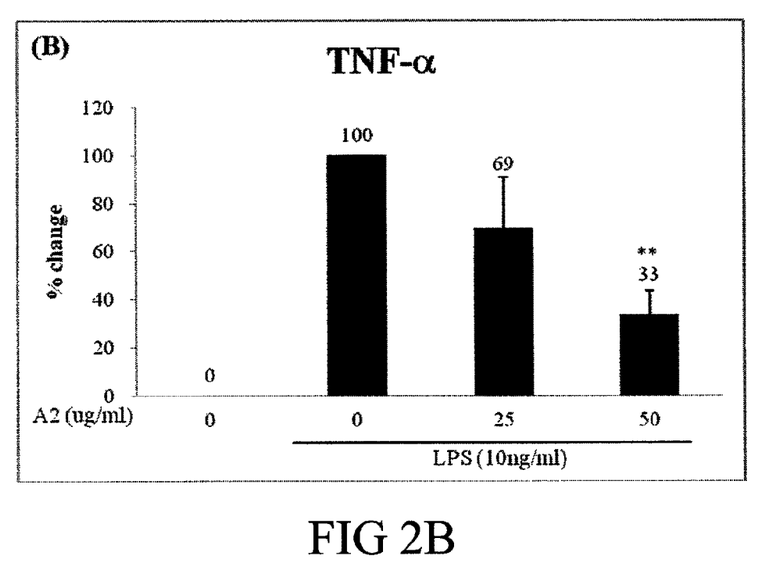
Figure 2C:
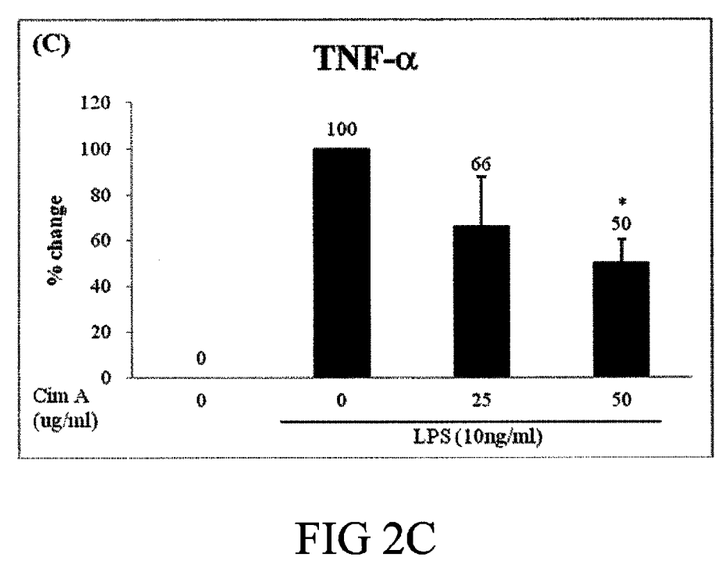
Figure 3:
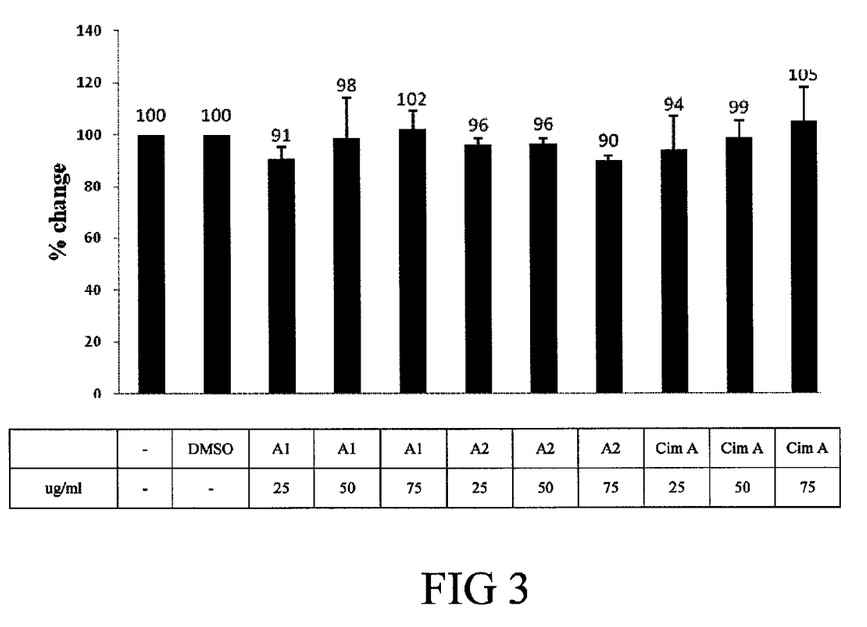
FIG. 3 shows that Compound A1, Compound A2 and Cim A have almost no cytotoxic effects. Incubation of PBMac cells with the compounds at various concentrations produces no significant difference in the metabolic activities of the cells, when compared to control. Cytotoxic effects of Compounds A1, A2 and Cim A (25-75 ug/ml) on PBMac are determined by MTT (3-[4,5-dimethylthiazol-2-yl]-2,5-diphenyltetrazolim bromide) assays over a time course of 48 h.

This Example shows that the compounds of the present invention have excellent anti-inflammatory activity. As shown in FIG. 1, Compound A1, Compound A2 and Cimiracemate A (Cim A) significantly inhibit the LPS-induced TNF-α protein production by 26±15%, 67±10% and 50±19% at LPS concentrations of 10 ng/ml, respectively (FIGS. 2A to C). Specifically, at a concentration of 50 μg/ml, the activity of Compound A2 in inhibiting LPS-induced TNF-α production is 34% higher than that of Cim A. Also, as shown in FIG. 3, Compound A1, Compound A2 and Cim A have almost no cytotoxic effects.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about", where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

REFERENCES

1. Aggarwal B B, Shishodia S, Sandur S K, Pandey M K, Sethi G. Inflammation and cancer: how hot is the link? Biochem Pharmacol. 2006; 72:1605-1621.
2. Woodworth C D, McMullin E, Iglesias M, Plowman G D. Interleukin 1 alpha and tumor necrosis factor alpha stimulate autocrine amphiregulin expression and proliferation of human papillomavirus-immortalized and carcinoma-derived cervical epithelial cells. Proc Natl Acad Sci U S A. 1995; 92:2840-2844.
3. Montesano R, Soulie P, Eble J A, Carrozzino F. Tumour necrosis factor alpha confers an invasive, transformed phenotype on mammary epithelial cells. J Cell Sci. 2005; 118:3487-3500.
4. Cheng S M, Xing B, Li J C, Cheung B K, Lau A S. Interferon-gamma regulation of TNFalpha-induced matrix metalloproteinase 3 expression and migration of human glioma T98G cells. Int J. Cancer. 2007; 121:1190-1196.
5. van der Poll T, Opal S M. Host-pathogen interactions in sepsis. Lancet Infect Dis. 2008; 8:32-43.
6. Raetz C R. Biochemistry of endotoxins. Annu Rev Biochem. 1990; 59:129-170.
7. Bone R C. Gram-negative sepsis. Background, clinical features, and intervention. Chest. 1991; 100:802-808.
8. Raetz C R, Ulevitch R J, Wright S D, Sibley C H, Ding A, Nathan C F. Gram-negative endotoxin: an extraordinary lipid with profound effects on eukaryotic signal transduction. Faseb J. 1991; 5:2652-2660.
9. Tracey K J, Cerami A. Tumor necrosis factor: a pleiotropic cytokine and therapeutic target. Annu Rev Med. 1994; 45:491-503.
10. Shakhov A N, Collart M A, Vassalli P, Nedospasov S A, Jongeneel C V. Kappa B-type enhancers are involved in lipopolysaccharide-mediated transcriptional activation of the tumor necrosis factor alpha gene in primary macrophages. J Exp Med. 1990; 171:35-47.
11. Ziegler-Heitbrock H W, Sternsdorf T, Liese J, et al. Pyrrolidine dithiocarbamate inhibits NF-kappa B mobilization and TNF production in human monocytes. J. Immunol. 1993; 151:6986-6993.
12. Trede N S, Tsytsykova A V, Chatila T, Goldfeld A E, Geha R S. Transcriptional activation of the human TNF-alpha promoter by superantigen in human monocytic cells: role of NF-kappa B. J. Immunol. 1995; 155:902-908.
13. Cheung B K, Lee D C, Li J C, Lau Y L, Lau A S. A role for double-stranded RNA-activated protein kinase PKR in *Mycobacterium*-induced cytokine expression. J. Immunol. 2005; 175:7218-7225.
14. Li J C, Lee D C, Cheung B K, Lau A S. Mechanisms for HIV Tat upregulation of IL-10 and other cytokine expression: kinase signaling and PKR-mediated immune response. FEBS Lett. 2005; 579:3055-3062.
15. Lee D C, Cheung C Y, Law A H, Mok C K, Peiris M, Lau A S. p38 mitogen-activated protein kinase-dependent hyperinduction of tumor necrosis factor alpha expression in response to avian influenza virus H5N1. J. Virol. 2005; 79:10147-10154.
16. Davis R J. The mitogen-activated protein kinase signal transduction pathway. J Biol. Chem. 1993; 268:14553-14556.
17. Su B, Karin M. Mitogen-activated protein kinase cascades and regulation of gene expression. Curr Opin Immunol. 1996; 8:402-411.

18. Chan-Hui P Y, Weaver R. Human mitogen-activated protein kinase kinase kinase mediates the stress-induced activation of mitogen-activated protein kinase cascades. Biochem J. 1998; 336 (Pt 3):599-609.
19. Herlaar E, Brown Z. p38 MAPK signalling cascades in inflammatory disease. Mol Med Today. 1999; 5:439-447.
20. Ichijo H. From receptors to stress-activated MAP kinases. Oncogene. 1999; 18:6087-6093.
21. Pando M P, Verma I M. Signal-dependent and -independent degradation of free and NF-kappa B-bound IkappaBalpha. J Biol. Chem. 2000; 275:21278-21286.
22. Abate A, Oberle S, Schroder H. Lipopolysaccharide-induced expression of cyclooxygenase-2 in mouse macrophages is inhibited by chloromethylketones and a direct inhibitor of NF-kappa B translocation. Prostaglandins Other Lipid Mediat. 1998; 56:277-290.
23. Chen F, Castranova V, Shi X, Demers L M. New insights into the role of nuclear factor-kappaB, a ubiquitous transcription factor in the initiation of diseases. Clin Chem. 1999; 45:7-17.
24. Panes J, Gomollon F, Taxonera C, Hinojosa J, Clofent J, Nos P. Crohn's disease: a review of current treatment with a focus on biologics. Drugs. 2007; 67:2511-2537.
25. Saunders B M, Britton W J. Life and death in the granuloma: immunopathology of tuberculosis. Immunol Cell Biol. 2007; 85:103-111.
26. Clay H, Volkman H E, Ramakrishnan L. Tumor necrosis factor signaling mediates resistance to mycobacteria by inhibiting bacterial growth and macrophage death. Immunity. 2008; 29:283-294.
27. Ohlsson K, Bjork P, Bergenfeldt M, Hageman R, Thompson R C. Interleukin-1 receptor antagonist reduces mortality from endotoxin shock. Nature. 1990; 348:550-552.
28. Tracey K J, Fong Y, Hesse D G, et al. Anti-cachectin/TNF monoclonal antibodies prevent septic shock during lethal bacteraemia. Nature. 1987; 330:662-664.
29. Schett G. Review: Immune cells and mediators of inflammatory arthritis. Autoimmunity. 2008; 41:224-229.

We claim:
1. A method for reducing inflammation, wherein said method comprises administering to a subject in need thereof, 50-75 µg/ml of compound A2

2. The method, according to claim 1, wherein TNF-α activity is inhibited.
3. The method, according to claim 1, wherein the subject has inflammation associated with infection, an environmental toxin, an autoimmune condition, cardiovascular disease, intestinal inflammation, allergy, graft rejection, pathological immune cell proliferation or activity, and/or respiratory inflammation.
4. The method, according to claim 1, wherein the subject has inflammation associated with rheumatoid arthritis, psoriasis, cardiovascular disease, inflammatory bowel disorder, septic shock and graft rejection.
5. The method, according to claim 1, wherein the subject is a human.

* * * * *

UNITED STATES PATENT AND TRADEMARK OFFICE
CERTIFICATE OF CORRECTION

PATENT NO. : 9,216,942 B2
APPLICATION NO. : 13/790707
DATED : December 22, 2015
INVENTOR(S) : Allan Sik Yin Lau et al.

Page 1 of 1

It is certified that error appears in the above-identified patent and that said Letters Patent is hereby corrected as shown below:

In The Specification

Column 2,
Line 26, "TNF-αproduction" should read --TNF-α production--.
Lines 42-43, "anti-TNF-αantibody" should read --anti-TNF-α antibody--.

Column 8,
Line 5, "Rx is a" should read --$R_x$ is a--.
Line 6, "Rx is a" should read --$R_x$ is a--.

Column 15,
Line 51, "fog ululated" should read --formulated--.

In The Claims

Column 20,
Lines 1-24,

" should read --  --.

Signed and Sealed this
Twenty-third Day of August, 2016

Michelle K. Lee
*Director of the United States Patent and Trademark Office*